United States Patent [19]

Alderman

[11] Patent Number: 5,074,901

[45] Date of Patent: Dec. 24, 1991

[54] COMPOSITION DERIVED FROM SEA WATER FOR THE TREATMENT OF VEGETATION AND ITS METHOD OF PRODUCTION

[76] Inventor: Norman E. Alderman, 13 Woodland Pl., Great Neck, N.Y. 11021

[21] Appl. No.: 334,677

[22] Filed: Apr. 6, 1989

[51] Int. Cl.⁵ .............................................. A01N 25/00
[52] U.S. Cl. ........................................................ 71/65
[58] Field of Search .................................... 71/65, 128

[56] References Cited

PUBLICATIONS

Frear, Donald, *Chemistry, of Insecticides, Fungicides & Herbicides,* 2nd ed., 1948, p. 311.
*CRC Handbook of Chemistry and Physics,* 58th ed, 1977, p. F-203.

*Primary Examiner*—Allen J. Robinson
*Assistant Examiner*—S. Mark Clardy
*Attorney, Agent, or Firm*—Bauer & Schaffer

[57] ABSTRACT

There is disclosed a LIQUOR useful as a natural herbicide and also, when diluted with water, useful as a plant micronutrient.

6 Claims, No Drawings

COMPOSITION DERIVED FROM SEA WATER FOR THE TREATMENT OF VEGETATION AND ITS METHOD OF PRODUCTION

The present invention relates to a LIQUOR, a method for making the same, and its use as a herbicide and/or a plant micronutrient, depending on dilution.

BACKGROUND OF THE INVENTION

Sea solids useful as fertilizer are known from U.S. Pat. No. 3,071,457 to Murray. In addition, the use of nutrient sea solids in hydroponic farming is disclosed in Murray's U.S. Pat. No. 3,250,606. According to the teachings of these patents, precipitated sea solids are harvested and used as a plant nutrient or fertilizer.

On the other hand, U.S. Pat. No. 3,770,410 discloses the production of potassium polyphosphates from a phosphoric acid sludge by heating the sludge to eliminate most of the water and then adding a salt mixture thereto to make a fertilizer.

Soilless culture of plants using sea water which is chemically modified with non-natural substances to change its composition is disclosed in U.S. Pat. No. 2,713,741. U.S. Pat. No. 3,640,695 and U.S. Pat. No. 3,332,767 disclose processes for converting mineralized water into irrigation water, by distillation and similar treatment.

U.S. Pat. No. 2,934,419 deals with the conversion of sea water into a solid fertilizer. U.S. Pat. No. 2,663,628 discloses a method of making a lignin fertilizer base using a cooking liquor as a component thereof. U.S. Pat. Nos. 4,450,001; 4,334,910; 4,382,013; 4,508,559; and 4,125,392 disclose similar compositions to regulate plant growth.

All of these known methods and their products fall into one of two categories. Firstly, sea solids are precipitated, removed and used as such. Secondly, the water of the starting material is distilled and used as fresh water. In the first instance, the resultant product is nothing more than a mixture of chemicals derived from sea water; in the second instance, the resultant product is pure water.

None of the prior art disclose the use of a LIQUOR containing water and salts, in which the ratios of the mineral salts to each other and to the remaining water are different from the ratios of such salts in the initial natural sea water. The resultant LIQUOR thus naturally altered from its initial state functions per se as a natural herbicide and also, in dilute aqueous concentrations, as a natural micronutrient. As used herein, the term "LIQUOR" defines the resultant product in which the ratios of salt are modified as disclosed and is to be distinguished from natural sea water as well as from a merely concentrated solution.

As will be explained hereinafter, the undiluted LIQUOR of the present invention is a swift, highly effective natural herbicide even when used in small amounts and may be applied directly to offending and deleterious growths without affecting any surrounding desirable vegetation. On the other hand, when highly diluted with fresh water, the LIQUOR of the present invention provides a totally unexpected and unobviously effective nutrient, by means of which the growth of desirable vegetation is enhanced and increased with rapidity and substantive benefit to the size, taste, appearance and the like of the vegetation. A further unexpected and unobvious result lies in the fact that the LIQUOR acts as a preservative in that the fruit of such vegetation lasts for a longer time after being picked. Thus, having a longer shelf life and transport life.

The noted benefits and advantages of the invention will be apparent from the following disclosure.

SUMMARY OF THE INVENTION

According to the present invention, natural sea water is subjected to conditions suitable to evaporate a portion of the water therefrom and simultaneously to precipitate a portion of the mineral salts dissolved therein so that the amount of such mineral salts remaining in the resulting LIQUOR differs from the amount of mineral salts contained in the natural sea water in proportion both to itself and to the remaining water. Thus, after the precipitate is removed, the resultant LIQUOR is not a mere concentrate of the natural sea water, but an unexpected mixture of water and salt capable of being used per se as a natural herbicide or diluted sufficiently with fresh water as a natural micronutrient.

More specifically, the present invention provides a method comprising the steps of subjecting a quantity of natural sea water to evaporation for a period of time sufficient to drive off a substantial portion of its water content and to precipitate a portion of the mineral salts dissolved in such natural sea water, thereby forming a LIQUOR containing dissolved mineral salts in ratios to each other and to the water different from those in the initial sea water; separating the remaining LIQUOR from the precipitated solid material (mineral salts); and recovering the LIQUOR.

Still further, in accordance with the present invention, deleterious vegetation can be destroyed or eradicated by applying to the same the LIQUOR described above in an amount effective to accomplish such result. On the other hand, when the above described LIQUOR is diluted sufficiently with fresh water, it may be applied to vegetation as a natural plant micronutrient when utilized in an amount effective to enhance in a significant and unobvious manner, the growth, appearance, and the like of the plant to which it is applied.

DESCRIPTION OF THE INVENTION

In general, the production of LIQUOR according to the present invention can be simply performed by allowing natural sea water to rest in a shallow pan or the like until a quantity of the water evaporates and a layer of precipitate scum is produced on the surface of the remaining natural sea water. The precipitate is then removed, the remaining natural sea water decanted, and the resultant used as the LIQUOR.

For example, shallow pans are filled to the brim with natural sea water and allowed to stand under conditions so that the dissolved mineral salts appear as a precipitate on the surface of the remaining natural sea water. Such precipitate is separated from the remaining natural sea water, which comprises the LIQUOR and can be decanted and bottled. The LIQUOR may first be filtered to remove any large particles and similar contaminants. In general, a quantity of about 5680 ml. of such initial natural sea water in two pans (e.g. shallow 3 quart, 13×9×2 inches) is reduced to about 230 ml. (an actual reduction of between 90% to 95% of volume) to provide the LIQUOR. This LIQUOR contains approximately 26% by weight of dissolved mineral salts in comparison to about 3.5% of mineral salts dissolved in the natural sea water, and has a substantially neutral pH.

The process may be enhanced by allowing the natural sea water to be moderately heated, with a gas or electric heater to elevate its temperature to induce evaporation, but not to boil the same. Also, the natural sea water may be placed in a vacuum environment to increase the rate of evaporation.

Because of the relatively constant rate of evaporation induced by the low heat, or the ambient external heat and the different rates of precipitation of the mineral salts contained in the natural sea water, the remaining LIQUOR contains dissolved mineral salts in ratios to each other, different from those in the original natural sea water. Such LIQUOR comprises a natural herbicide per se and exerts a herbicidal effect on vegetation when applied thereto in an amount effective to eradicate undesired or unwanted specimens.

While natural sea waters throughout the world vary somewhat in the amount of dissolved mineral salts, there is a relative similarity among them. New York sea water is generally typical of ocean waters. The analysis of sea water is well established, as evidenced by the data set forth on Pages 176 and 177 of "The Oceans" (1942) by Sverdrup, Johnson, and Fleming.

A LIQUOR made from New York sea water in accordance with the present invention has the following analysis with respect to the mineral salts dissolved therein:

|  | ppm.(mg./l.) |
|---|---|
| Nitrate | <1.0 |
| Sodium | 2141.69 |
| Aluminum | 0.21 |
| Cadium | <0.01 |
| Chromium Total | 0.02 |
| Chromium Hexavalent | <0.01 |
| Copper | 0.31 |
| Iron | 0.37 |
| Nickel | 0.02 |
| Lead | 0.05 |
| Silver | 0.19 |
| Zinc | <0.01 |
| Manganese | 0.05 |
| Chloride | 2373.2 |
| Sulfate | 4.11 |
| Fluoride | 0.26 |
| Calcium | 6.45 |
| Barium | 0.07 |
| Magnesium | 1.69 |
| Ammonia | 0.15 | and had a pH of 6.87.

The present LIQUOR is effective, undiluted, as a natural herbicide, as already indicated. It has also been found that the addition of a slight amount of fresh water to the LIQUOR does not reduce its effectiveness as a herbicide. A small amount of a wetting agent may be used to enhance the spread of the same. This LIQUOR may be applied directly to the root system and/or to the leaf system of the plant or vegetation to be killed by spraying or other suitable means.

As previously mentioned, the LIQUOR is also useful as a plant nutrient when it is highly diluted with fresh water. Broadly, the LIQUOR should be present in an aqueous diluent in an amount at least sufficient to have a micronutrient effect on plant life, i.e., up to about 3800 parts of fresh water to 1 part of LIQUOR by volume. In general, however, the LIQUOR is present in the aqueous diluent in a concentration of about 0.5 ml. to about 1.0 ml. per gallon to be useful as a plant nutrient. It has been found that for fruit plants the lower range of concentration is best, while for green leaf plants and the like, the upper range of concentration (i.e. 1.0 ml. per gallon) is generally preferred. Application of such diluted LIQUOR may be made to the root and/or the leaf systems by spraying or otherwise as desired.

EXAMPLES OF USE

In order to illustrate the present invention more fully, the following examples are set forth. In the examples all values with respect to amounts and ratios are the same as those set forth above, unless otherwise indicated.

Example I

As a Herbicide

Dandelion plants in a New York suburb were treated by spraying the base of the plants with undiluted LIQUOR. The spray was made to wet the soil but not to saturate it. Within one day signs of morbidity were observed; and within three days the dandelions were dead.

Such LIQUOR was similarly applied to weeds known as Nut Grass and "Torpedo grass" in Lake Worth, Florida, with similar results.

The foregoing procedures were respectively repeated 5 to 10 times over a period of several days on similar patches of dandelions and Torpedo grass, nut grass, crab grass and the like.

In each instance, the present LIQUOR herbicide was selective and attacked only those plants to which it was applied and did not spread or leach outwardly and cause harm to any surrounding desired vegetation.

It must be noted that the LIQUOR is made from a product of nature and does not injure or affect the aquifer as previously known commercial herbicides or pesticides do. It is made from a natural product and does not have a carcinogenic background.

Example II

As A Nutrient

The LIQUOR was diluted in a ratio of 1 ml. to 1 gallon of fresh tap water, the diluted solution being applied to tomato and strawberry plants on commercial farms in Lake Worth, Florida during the months of January through April. The plants were only a part of the entire field of plants and were located in a partially shaded area. The diluted LIQUOR was applied by spraying directly to the leaf portions of the plants and to the soil surrounding the plants.

Within several days it became obvious that the plants exhibited improved color and strength. The plants grew more rapidly than plants not so treated. The treated crop was larger in size and weight and better resisted insect blight; and the fruit, when harvested, were sweeter and tasted better than those not so treated. This occurred notwithstanding the partial shade and the winter growth season. The results, i.e., fruit of this experiment were taste tested in comparison to non-treated fruit (control) by an impartial panel. Of the persons responding, about 70% liked the experimental tomato best, and only 25% liked the control tomato best, while the rest could not differentiate between the experimental fruit or the control.

An unexpected and unanticipated result was observed during recent tests with strawberries. A large number of the control strawberries displayed extensive mold formation and softening and had to be discarded nine to eleven days after picking even when kept under refrigerated conditions. On the other hand, strawberries treated with the LIQUOR of the present invention lasted over 3 weeks and few if any, were lost to mold, etc. Therefore, a natural preservative feature is apparent from the present invention.

The present invention presents many other advantages. For example, the LIQUOR is made from readily available natural starting materials; and the method for making the same is simple and straightforward, requiring no special expensive equipment or the use of non-material chemical components. Moreover, the LIQUOR so prepared can be readily made useful as a plant nutrient by simple dilution with water or the like; and whether used as a herbicide or a plant nutrient, the LIQUOR may be applied in any convenient manner. Numerous other advantages of the invention will be readily apparent to those skilled in the art.

It is to be understood that numerous modifications and variations of this invention may be made without departing from the spirit and scope of the invention, and consequently this invention should not be limited to the described embodiments except as defined in the appended claims.

What is claimed is:

1. A process of treating vegetation to eliminate unwanted specimens, which comprises applying to such vegetation a LIQUOR in a quantity effective to eradicate the unwanted specimens, said LIQUOR having been obtained by subjecting an initial quantity of natural sea water to conditions suitable to evaporate a portion of the water from said initial quantity and simultaneously to precipitate a portion of the mineral salts dissolved in the natural sea water in said initial quantity and separating the mineral salt precipitate from the resulting LIQUOR so that the amount of mineral salts remaining in the LIQUOR is less than the amount contained in the initial quantity of natural sea water, and the ratios of the mineral salts to each other in said LIQUOR are different from the ratios of such mineral salts to each other, both in the initial quantity of natural sea water and in the separated mineral salt precipitate.

2. A process according to claim 1, in which the LIQUOR is obtained by heating the natural sea water to a temperature above atmospheric without boiling.

3. A process according to claim 1, in which the LIQUOR is applied to the vegetation by spraying.

4. A process according to claim 1, in which the unwanted specimens of vegetation comprises weeds.

5. A process according to claim 1, in which the LIQUOR contains about 26% by weight of such mineral salts.

6. A method of controlling deleterious vegetation, which comprises applying to said vegetation a herbicidal LIQUOR, as defined in claim 1, in a quantity effective to eradicate said vegetation.

* * * * *